US012152969B2

(12) United States Patent
Chiang et al.

(10) Patent No.: US 12,152,969 B2
(45) Date of Patent: Nov. 26, 2024

(54) METHOD FOR PREPARATION OF TISSUE SECTIONS

(71) Applicant: JelloX Biotech Inc., Hsinchu (TW)

(72) Inventors: Ann-Shyn Chiang, Hsinchu (TW); Dah-Tsyr Chang, Hsinchu (TW); I-Ching Wang, Hsinchu (TW); Jia-Ling Yang, Hsinchu (TW); Shun-Chi Wu, Hsinchu (TW); Yen-Yin Lin, Hsinchu (TW); Yu-Chieh Lin, Hsinchu (TW)

(*) Notice: Subject to any disclaimer, the term of this patent is extended or adjusted under 35 U.S.C. 154(b) by 514 days.

(21) Appl. No.: 17/140,155

(22) Filed: Jan. 4, 2021

(65) Prior Publication Data

US 2021/0231540 A1 Jul. 29, 2021

Related U.S. Application Data

(63) Continuation-in-part of application No. 16/891,101, filed on Jun. 3, 2020.

(Continued)

(51) Int. Cl.
*G01N 1/30* (2006.01)
*G01N 21/64* (2006.01)
*G01N 33/483* (2006.01)

(52) U.S. Cl.
CPC .......... *G01N 1/30* (2013.01); *G01N 21/6428* (2013.01); *G01N 21/6458* (2013.01);
(Continued)

(58) Field of Classification Search
None
See application file for complete search history.

(56) References Cited

U.S. PATENT DOCUMENTS 10,591,392 B2 * 3/2020 Torres ................ G01N 33/4833
11,333,588 B1 * 5/2022 Tian ......................... G01N 1/36
(Continued)

FOREIGN PATENT DOCUMENTS

JP 2019094753 * 6/2019
TW 594593 6/2004
(Continued)

OTHER PUBLICATIONS

JP,2019-138697 English machine translation ; Hiroko et al Aug. 22, 2019 (Year: 2019).*
(Continued)

*Primary Examiner* — Nancy Bitar (57) ABSTRACT

Provided is a method for preparing a tissue section, including treating a tissue specimen with a clearing agent and at least one labeling agent to obtain a cleared and labeled tissue specimen; generating a three-dimensional (3D) image of the cleared and labeled tissue specimen; performing an image slicing procedure on the 3D image to generate a plurality of two-dimensional (2D) images; identifying a target 2D image among the plurality of 2D images to obtain a distance value of D1, which indicates the distance between the target 2D image and a predetermined surface of the 3D image; preparing a hardened tissue specimen from the cleared and labeled tissue specimen; and cutting the hardened tissue specimen near a predetermined site to obtain a tissue section, wherein the distance between the predetermined site and a surface of the hardened tissue specimen corresponding to the predetermined surface of the 3D image is D1.

13 Claims, 11 Drawing Sheets

Related U.S. Application Data (60) Provisional application No. 62/957,308, filed on Jan. 5, 2020, provisional application No. 62/856,741, filed on Jun. 4, 2019.

(52) U.S. Cl.
CPC ... *G01N 33/4833* (2013.01); *G01N 2001/305* (2013.01); *G01N 2021/6439* (2013.01)

(56) References Cited

U.S. PATENT DOCUMENTS

| | | | |
|---|---|---|---|
| 11,913,870 B2 * | 2/2024 | Hart | G01N 15/147 |
| 2007/0135999 A1 * | 6/2007 | Kolatt | G06V 20/695 |
| | | | 702/19 |
| 2014/0306952 A1 * | 10/2014 | Oka | G06T 15/10 |
| | | | 345/419 |
| 2016/0003715 A1 * | 1/2016 | Torres | G01N 33/4833 |
| | | | 435/40.52 |
| 2017/0262984 A1 * | 9/2017 | Barnes | G06V 20/698 |
| 2017/0370810 A1 * | 12/2017 | Miyawaki | G01N 33/4833 |

FOREIGN PATENT DOCUMENTS

| | | |
|---|---|---|
| TW | I372859 B | 9/2012 |
| TW | I396142 B | 5/2013 |
| TW | I425201 B | 2/2014 |
| TW | I493167 B | 7/2015 |
| TW | 202102832 A | 1/2021 |

OTHER PUBLICATIONS

Office Action and search report from the Taiwan Intellectual Property Office, Jan. 10, 2022.

* cited by examiner

METHOD FOR PREPARATION OF TISSUE SECTIONS

CROSS REFERENCE TO RELATED APPLICATIONS

This application claims priority to U.S. Provisional Application Ser. No. 62/957,308, filed on Jan. 5, 2020; and this application is a continuation-in-part of U.S. patent application Ser. No. 16/891,101, filed on Jun. 3, 2020, which claims priority to U.S. Provisional Application Ser. No. 62/856,741, filed on Jun. 4, 2019, and incorporates the disclosure of all the above-identified applications by reference.

FIELD OF THE INVENTION

This invention relates to a biological sample preparation method, and more particularly, to a method for preparing tissue sections by utilizing a three-dimensional (3D) histopathology imaging method.

BACKGROUND OF THE INVENTION

Histopathology refers to microscopic examination of tissue in order to study the manifestations of disease. Histopathology can be more definitely defined in clinical medicine and refers to the examination of a biopsy or a surgical specimen by a pathologist, after the specimen has been processed and histological sections have been placed onto glass slides.

Figure 1:
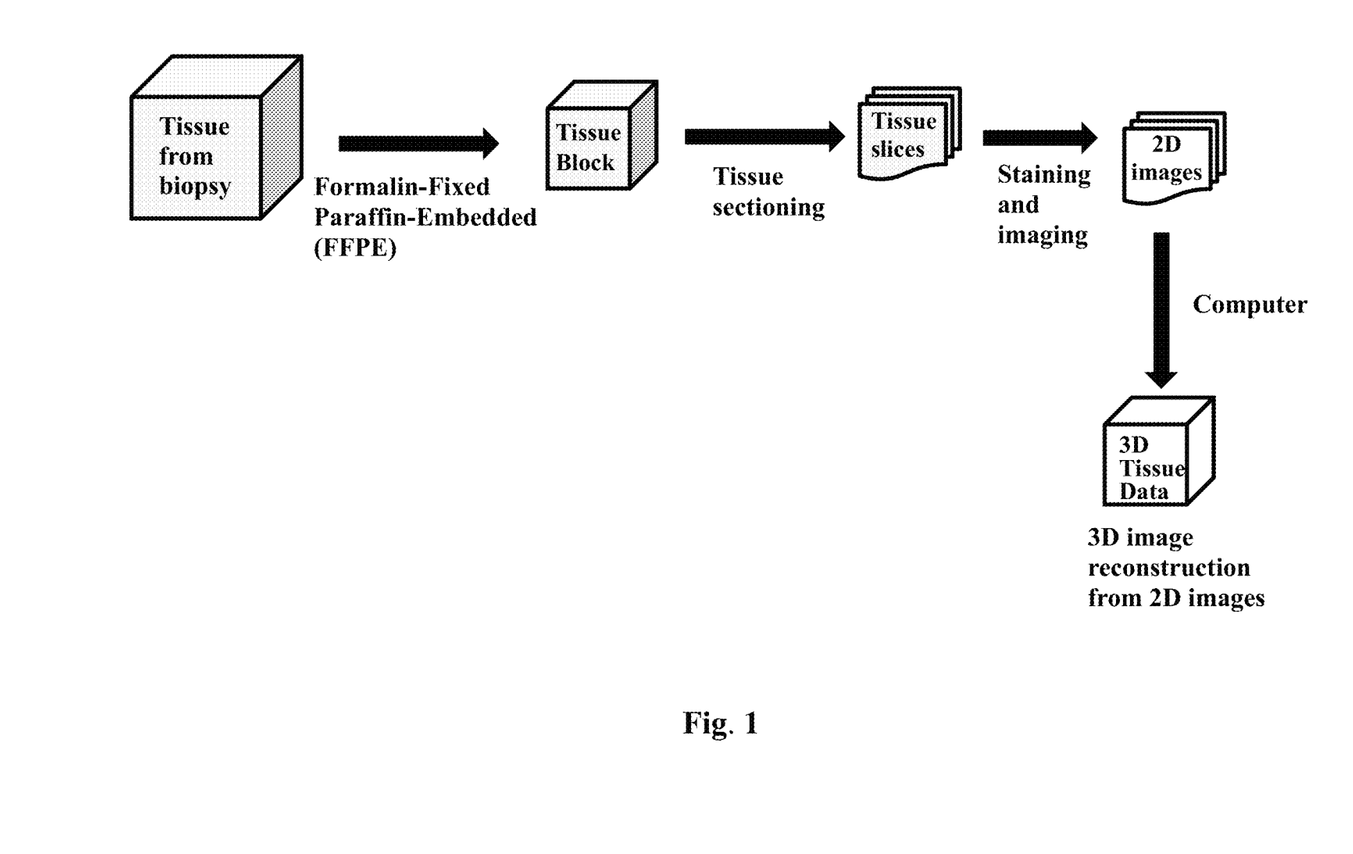
FIG. 1 illustrates one conventional 3D histopathology imaging process.

3D histopathology image involves the use of current technologies, such as microscopy and computer imaging systems, to facilitate conventional microscopic examination. FIG. 1 illustrates one of the conventional techniques for conducting a 3D histopathology. As shown in FIG. 1, a tissue specimen is obtained through biopsy. The tissue may be lung or kidney tissue. The tissue specimen is next performed with a so-called formalin-fixed paraffin-embedded (FFPE) process to form a tissue block. The tissue block is then cut into slices or sections, each being about 3-5 μm in thickness. Each slice is then stained, and a microscopy equipped with a camera is utilized to image the slices and to generate 2D images of each slice. These 2D images will be sent to and processed by a computer. The computer gathers and processes the 2D images to reconstruct a 3D image from the 2D images. This conventional technique however causes a 2 μm image loss between two successive 2D images since the tissue was sliced into pieces at the beginning.

Figure 2:
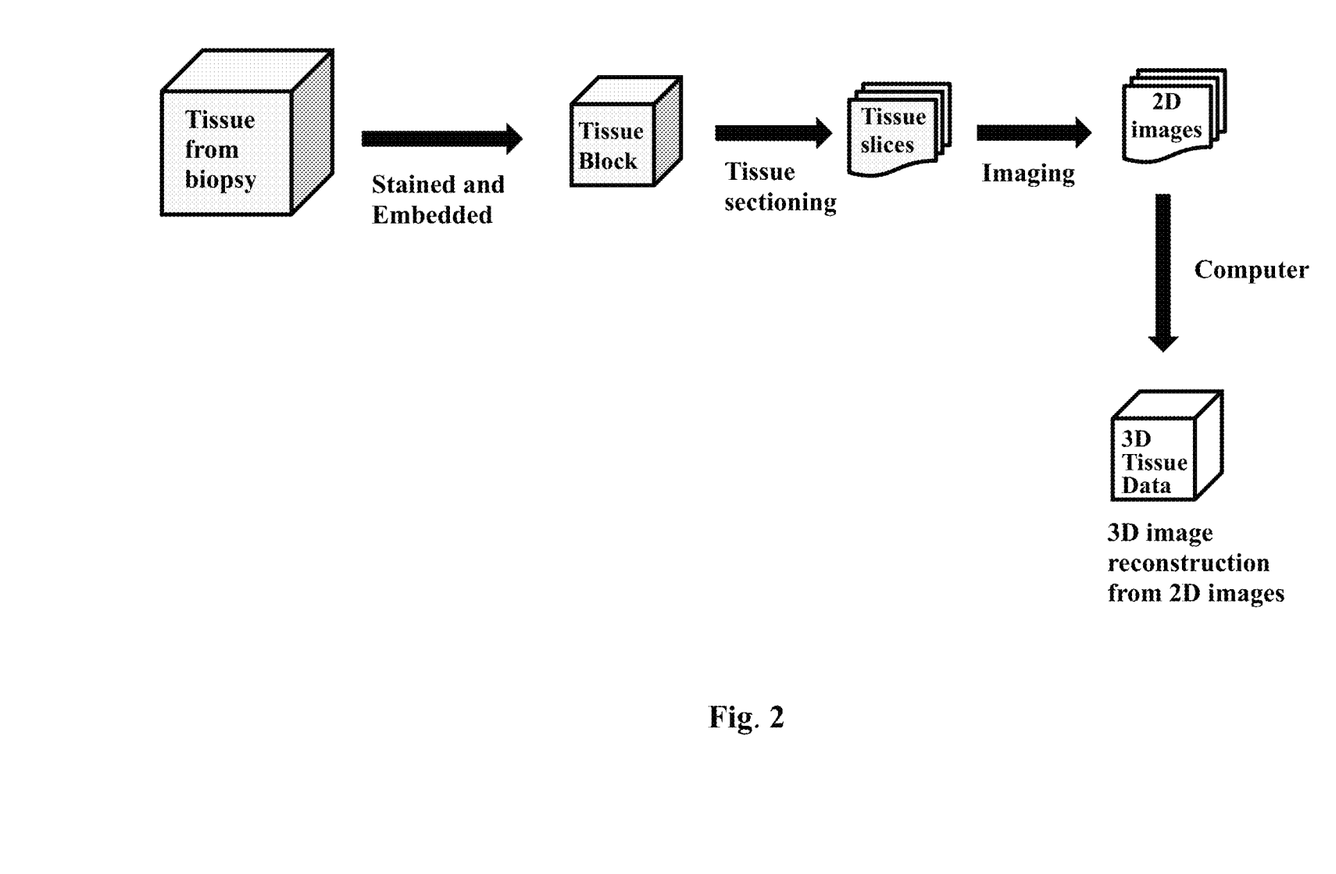
FIG. 2 illustrates another conventional 3D histopathology imaging process.

FIG. 2 illustrates another conventional technique for obtaining a 3D histopathology imaging. Likewise, a tissue is obtained through biopsy, but the tissue is next stained and embedded in paraffin to form a tissue block. The ensuing slicing process, 2D imaging and 3D reconstructing processes are alike to those as described in FIG. 1 and are thus omitted for relevant descriptions. Though the effectiveness of this technique is improved a bit, it however still exhibits a 1-2 μm image loss between two successive 2D images, and such image loss is also attributable to the slicing process. Accordingly, how to reduce the image loss is a pending problem that needs to be solved.

Another issue arising from said conventional histopathology is that blind sectioning during preparation of tissue sections might destroy the integrity of key morphological features in the tissue, rendering the resultant tissue sections less representative of their origins. Furthermore, it typically takes hundreds rounds of cutting of one biopsy specimen and hundreds rounds of staining to obtain hundreds of stained tissue sections for subsequent examination, yet only a few of these sections reveal definitive abnormal results that can serve as diagnostic basis. It is obvious that in this scenario, excess time and chemicals are spent to prepare hundreds of tissue sections that have no further applications. Accordingly, it is necessary to develop a new method of preparing tissue sections to improve the accuracy and efficiency of clinical diagnosis.

SUMMARY OF THE INVENTION

In one aspect, the present invention provides a method for preparing a tissue section directly from a particular portion in a tissue specimen through utilization of a 3D histopathology imaging method with reduced image losses. More specifically, the method includes the steps of: (a) treating a tissue specimen with a clearing agent and at least one labeling agent for labeling a cellular component so as to obtain a cleared and labeled tissue specimen; (b) generating a 3D image of the cleared and labeled tissue specimen; (c) performing an image slicing procedure on the 3D image to generate a plurality of two-dimensional (2D) images; (d) identifying a target 2D image among the plurality of 2D images to obtain a distance value of D1, wherein D1 is the distance between the target 2D image and a predetermined surface of the 3D image; (e) preparing a hardened tissue specimen from the cleared and labeled tissue specimen; and (f) cutting the hardened tissue specimen near a predetermined site to obtain a tissue section, wherein the distance between the predetermined site and a surface of the hardened tissue specimen corresponding to the predetermined surface of the 3D image is D1. Through steps (a)-(c), which constitute the 3D histopathology imaging method, and steps (d)-(f), which apply the spatial information to physical cutting, the method of the present invention can efficiently produce tissue sections with increased representativeness.

In certain embodiments, the clearing agent is an aqueous clearing agent having a refractive index (RI) of 1.33-1.55, preferably 1.40-1.52, and more preferably 1.45-1.52. Treatment with such clearing agent causes a tissue specimen with a thickness of at least 200 μm to become sufficiently transparent while preventing tissue shrinkage or deformation and eliminating lipid removal. Since the structural integrity of the cleared tissue specimen is well preserved, the 3D image of said specimen provide more accurate morphological information. Moreover, fluorescent labeling of cell membrane or membrane associated proteins are compatible with such clearing agent, allowing detection of various marker proteins for many diseases, particularly marker proteins for cancers.

In certain embodiments, the labeling agent is a fluorescence dye, or a conjugate of a fluorescence dye and a molecular probe selected from the group consisting of an agonist, an antagonist, an antibody, an avidin, a nucleotide, a lipid nucleotide, and a toxin.

In certain embodiments, in step (a), the tissue specimen is embedded in an embedding material, which provides physical support to the tissue specimen. The embedding material may be an agarose gel or a hydrogel.

In certain embodiments, the labeling agent is removed from the cleared and labeled tissue specimen before step (e) or is removed from the tissue section after step (f). Once the labeling agent is removed, the tissue section may be further stained to obtain a stained tissue section. Tissue staining may be carried out by staining processes well-known in the art, for example, hematoxylin and eosin (H&E) staining, immunohistochemistry (IHC), immunofluorescence (IF) staining, and fluorescence in situ hybridization (FISH) staining.

In certain embodiments, the clearing agent and the labeling agent are included in a clearing composition, and the clearing composition further includes a permeating agent. In the clearing composition, the clearing agent includes a refractive index matching material selected from the group consisting of a radiocontrast agent, a monosaccharide, an oligosaccharide, and any combinations thereof. The permeating agent is preferably a surfactant selected from the group consisting of Triton X-100, Tween-20, Tween-80, sodium dodecyl sulfate (SDS), n-dodecyl-β-d-maltoside (DDM), urea, 3-[(3-cholamidopropyl) dimethylammonio]-1-propanesulfonate (CHAPS), sodium deoxycholate, and any combinations thereof.

In certain embodiments, the 3D image is generated by using a microscopy such as laser scanning microscopy to scan the cleared and labeled tissue specimen. The 3D image is a 3D model of the tissue specimen that can be further analysed three dimensionally by image slicing. During the image slicing procedure, the 3D image is sliced in different directions to generate a plurality of 2D image slices. Said image slicing may be conducted along one axis selected from three mutually perpendicular axes (referred to as an X-axis, a Y-axis and a Z-axis) of the 3D image.

In certain embodiments, the cellular component being labeled is a cell membrane, an organelle, or a biomolecule. The organelle may be a membrane-bound organelle such as cell nucleus or a non-membrane-bound organelle such as ribosome. The biomolecule may be a nucleic acid or a protein such as a disease-related protein. Due to the labeling, the structure or physiological condition of the tissue specimen can be revealed at cellular level and even molecular level, and thus one target 2D image that displays a particular characteristic can be identified among the plurality of 2D images. In certain embodiments, the target 2D image is identified by measuring an expression level of a biomolecule in each 2D image among the plurality of 2D images. In certain embodiments, the target 2D image is identified by measuring a proportion of cells with abnormal morphology (e.g., cell aggregate or cell invasion) relative to total cells in each 2D image among the plurality of 2D images.

The method disclosed herein may be performed on a platform including a 3D histopathology imaging system connected to a microtome. The 3D histopathology imaging system includes a microscopy and a processor. The microscopy is configured to establish a 3D image of a tissue specimen. The processor is configured to perform an image slicing procedure on the 3D image to generate a plurality of 2D images, to identify one target 2D image, and to yield a distance value of D1. The microtome may be a conventional microtome that can cut a specimen at a predetermined site.

The method disclosed herein enables direct preparation of tissue sections that best represents a diseased or susceptible tissue, thus saving time and chemicals required to prepare tissue slides while also reducing the space needed for slide storage. In addition, because the most representative portions in a tissue specimen can be identified prior to physical sectioning, it can be avoided to destroy these portions due to blind sectioning. Therefore, pathologists are capable to make more accurate diagnosis with the tissue sections prepared by this method, which facilitates physicians to determine appropriate treatments for each patient.

BRIEF DESCRIPTION OF THE DRAWINGS

The present invention will be apparent to those skilled in the art from the following detailed description of the preferred embodiments, with reference to the attached drawings, in which.

DETAILED DESCRIPTION OF THE PREFERRED EMBODIMENTS

Unless defined otherwise, all technical and scientific terms used herein have the same meanings as commonly understood by one skilled in the art to which this disclosure belongs. It will be further understood that the terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used herein, the singular forms "a", "an" and "the" include plural referents unless the context clearly indicates otherwise.

Numerical quantities given herein are approximate, and experimental values may vary within 20 percent, preferably within 10 percent, and most preferably within 5 percent.

Figure 3:
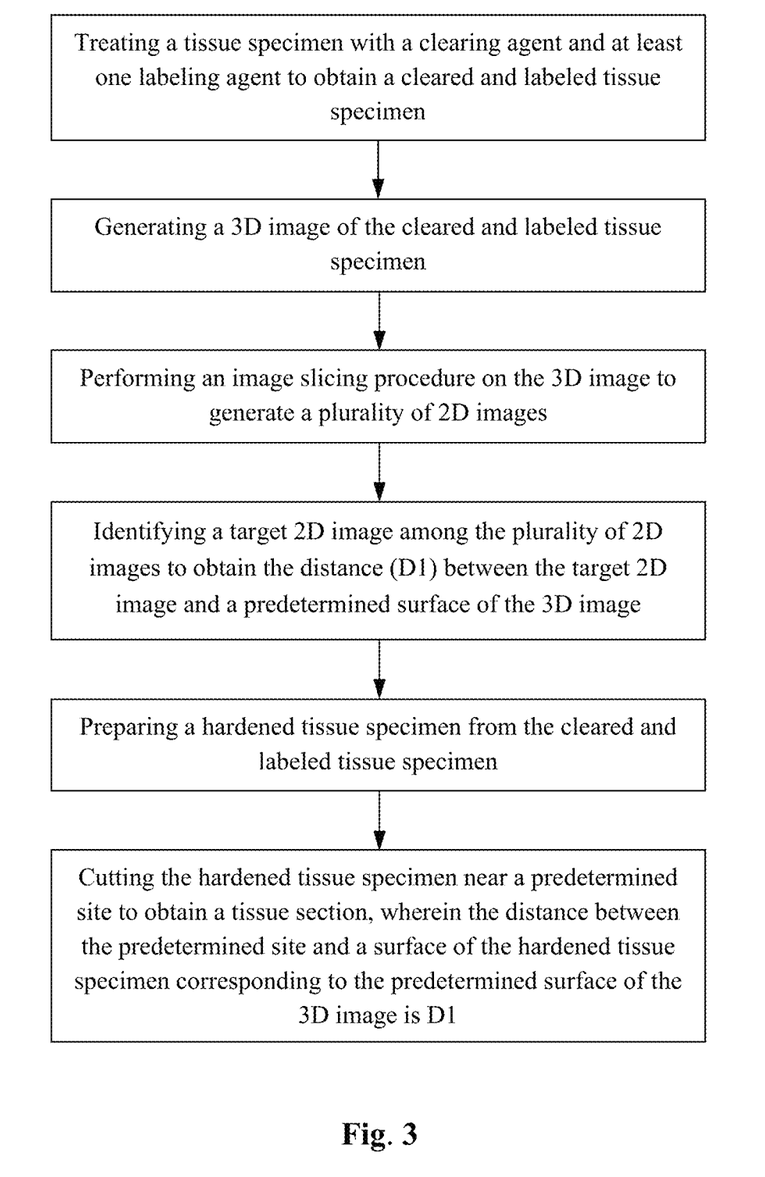
FIG. 3 is a flowchart illustrating the steps of the method disclosed herein.

As shown in FIG. 3, the method disclosed herein includes the steps of: (a) treating a tissue specimen with a clearing agent and at least one labeling agent for labeling a cellular component so as to obtain a cleared and labeled tissue specimen; (b) generating a 3D image of the cleared and labeled tissue specimen; (c) performing an image slicing procedure on the 3D image to generate a plurality of two-dimensional (2D) images; (d) identifying a target 2D image among the plurality of 2D images to obtain a distance value of D1, wherein D1 is the distance between the target 2D image and a predetermined surface of the 3D image; (e) preparing a hardened tissue specimen from the cleared and labeled tissue specimen; and (f) cutting the hardened tissue specimen near a predetermined site to obtain a tissue section, wherein the distance between the predetermined site and a surface of the hardened tissue specimen corresponding to the predetermined surface of the 3D image is D1.

The method of the invention begins with a tissue sample or specimen collected from a subject to be diagnosed. The subject refers to a mammal, including human or non-human, such as a primate, murine, dog, cat, cow, horse, rabbit, pig, or the like. Said subject, either already diseased or prone to disease, is usually subjected to a biopsy, which is a procedure to remove a piece of tissue from an individual's body such that the specimen can be subsequently analyzed to identify the presence and the extent of a disease. Various types of biopsies can be performed to obtain a tissue specimen to be examined following the disclosed method. Examples of biopsies include skin biopsy, endoscopic biopsy, needle biopsy, bone marrow biopsy, and surgical biopsy.

In step (a) of the disclosed method, the tissue specimen is treated with a clearing agent and at least one labeling agent for labeling a cellular component. This tissue clearing process renders the tissue specimen optically clear or transparent by homogenization of the various refractive indices of a tissue, resulting in reduced light scattering and improved light penetration. Hence, tissue clearing allows nearly no physical tissue sectioning prior to microscopic examination of thick tissue specimens with a thickness of about 150-250 µm, and thus reduces the possible artifacts resulting from tissue stretching, bending, and tearing.

In certain embodiments, the clearing agent is an aqueous clearing agent having a refractive index of 1.33-1.55, preferably 1.40-1.52, and more preferably 1.45-1.52. The clearing agent includes a solvent and a refractive index (RI) matching material. The solvent may be water, phosphate buffered saline (PBS; for example, 137 mM sodium chloride, 2.7 mM potassium chloride, 7.7 mM disodium hydrogen phosphate, and 1.47 mM potassium dihydrogen phosphate dissolved in water, pH 7.4), or other inorganic buffers. The aqueous clearing agent may be prepared by adding in water or PBS an RI matching material selected from the group consisting of glycerol, iohexol (also sold under the name Histodenz), formamide, triethanolamine, meglumine diatrizoate, and combinations thereof. The final concentration of the RI matching material in the aqueous clearing agent may vary between 30-70 wt %. Tissue clearing with such clearing agent may be carried out at room temperature for 2 to 12 hours, preferably for 2 to 8 hours, and more preferably for 2 to 4 hours.

In addition to be cleared, the tissue specimen is also to be labeled with at least one labeling agent for labeling a cellular component, such as cell membrane, cell nucleus, or a protein with a particular amino acid sequence or a particular modification or conformation. In certain embodiments, the labeling agent is a fluorescence dye, or a conjugate of a fluorescence dye and a molecular probe selected from the group consisting of an agonist, an antagonist, an antibody, an avidin, an oligonucleotide, a lipid nucleotide, and a toxin. Different kinds of labeling agents are suitable for labeling different targets. For example, cell nucleus may be labeled with propidium iodide (PI), 4',6-diamino-2-phenylindole (DAPI), SYTO-series of dyes (e.g., SYTO 16 and SYTO 40 purchased from Thermo Fisher Scientific), NucRed, or NucGreen. Membranous structures of cells may be labeled with a lipophilic fluorescence dye, such as Di series of dyes (e.g., DiD and DiR purchased from Invitrogen) and PKH series of dyes (e.g., PKH26 and PKH67 purchased from Merck). A marker protein for a disease may be labeled with a primary antibody and a secondary antibody, wherein the primary antibody can specifically bind the marker protein and the secondary antibody can recognize the primary antibody.

Step (a) may be accomplished by separately or concurrently contacting the tissue specimen with the clearing agent and the labeling agent. In some preferred embodiments, the clearing agent and the labeling agent are included in a clearing composition that further includes a permeating agent such that tissue clearing and labeling can be completed in one single step. In the clearing composition, the RI matching material is preferably selected from the group consisting of a radiocontrast agent (e.g., iodixanol), a monosaccharide (e.g., fructose), an oligosaccharide (e.g., sucrose), and any combinations thereof. The permeating agent is preferably a surfactant selected from the group consisting of Triton X-100, Tween-20, Tween-80, sodium dodecyl sulfate (SDS), n-dodecyl-β-d-maltoside (DDM), urea, 3-[(3-cholamidopropyl) dimethylammonio]-1-propanesulfonate (CHAPS), sodium deoxycholate, and any combinations thereof. The RI matching material may be at a concentration of 30 to 80% (w/v). The permeating agent mat be at a concentration of 0.1 to 2% (v/v). The labeling agent may be at a concentration of 100 ng/ml to 1 mg/mL.

The tissue specimen to be cleared and labeled may be either fresh or archival. In one embodiment, the tissue specimen is collected immediately from a portion of a patient's body, such as a solid tumor, and thus is in a fresh state. In another embodiment, the tissue specimen has been processed according to sample preparation methods well-known to one skilled in the art and is referred to as an archival specimen. The sample preparation methods may include the steps of fixation, dehydration, infiltration, and embedding. Fixation is a process to prevent decay and preserve tissue morphology in which a tissue specimen is immersed in a fixative such as formalin (4% formaldehyde by mass in buffered saline) at room temperature for typically 4-48 hours, depending on the size of the specimen. Dehydration is a process to remove water from the specimen by treating a fixed specimen with increasing concentrations of a dehydrant, for example, treatment with 70%, 95%, and 100% of an alcohol such as ethanol, followed by treatment with xylene. Infiltration is a process to allow an embedding medium such as resin or wax to permeate the specimen. One example of infiltration is placing a dehydrated specimen in a mixture of xylene and a molten wax such as paraffin wax heated to 56-60° C. Embedding is accomplished by transferring an infiltrated specimen in an embedding container, where the embedding medium such as molten paraffin wax is subsequently introduced around the specimen and cooled to form a hard block of tissue (also called tissue block). The archival specimen processed by fixation with formalin and embedding in paraffin is referred to as FFPE-treated.

In the case where the tissue specimen is fresh, the specimen may further be fixed with a fixative such as formalin at room temperature for 6 to 12 hours prior to the clearing and labeling step. Alternatively, when a FFPE-treated specimen is to be examined, it may be deparaffinized with xylene and alcohol at room temperature for 2 hours and 4-6 hours, respectively, prior to the clearing and labeling step.

During tissue clearing and labeling in step (a), the tissue specimen may be embedded in an embedding material such as an agarose gel or a hydrogel. The embedding provides physical support to the specimen. In one embodiment, an agarose gel is prepared from a warm aqueous solution containing 1-4% w/w agarose. In another embodiment, the hydrogel is prepared from a water dispersion of at least one natural or synthetic polymer which solidifies upon change in temperature, pH, salts, or irradiation. Examples of said polymer includes alginate, hyaluronates, and acrylamide-based polymers.

Next in step (b), a 3D image of the cleared and labeled tissue specimen is generated by microscopy. In certain embodiments, laser scanning microscopy is applied to obtain a plurality of successive 2D images of the cleared and labeled tissue specimen at different depths such that a 3D image is reconstructed from those 2D images. Examples of the laser scanning microscopy include laser scanning confocal microscopy (LSCM), two-photon microscopy, three-photon microscopy, and line-scanning confocal microscopy. Other microscopy involving scanning technologies such as spinning disk confocal microscopy or light-sheet microscopy may also be applied in the disclosed method to generate a 3D image of the tissue specimen. Therefore, the scope of the present invention should not be limited to laser scanning microscopy. Since the scanning is performed on an intact tissue specimen, in other words, the tissue specimen is scanned prior to being sliced into pieces, the 3D image obtained by the disclosed method has much less image losses.

Next in step (c), an image slicing procedure is performed on the 3D image to generate a plurality of 2D images. The image slicing procedure is a virtual slicing procedure, during which the 3D image is sliced into multiple virtual slices. Each image slice may be displayed on a monitor as a conventional 2D image, showing a cross-sectional view of the imaged tissue specimen. Virtual image slicing is well known in the field of image processing, and relevant descriptions regarding virtual image slicing is omitted for convenience.

The 3D image may be virtually sliced along an X-axis, a Y-axis, a Z-axis, or combinations thereof. In certain embodiments, the 3D image is sequentially sliced along the three axes to generate three batches of 2D images (i.e., multiple 2D images in the XY-plane, YZ-plane, and XZ-plane). The X-axis, Y-axis and Z-axis may be construed as coordinates in a Euclidean space, and the 3D image may be presented as a vector in the Euclidean space. In certain embodiments, the 3D image is virtually sliced along the three axes to generate a plurality of 2D images in the XY-plane, YZ-plane, and XZ-plane. The directions of the X-axis, Y-axis and Z-axis are not specifically restricted, except that the X-axis, Y-axis and Z-axis are perpendicular to one another. In other words, the X-axis, Y-axis and Z-axis collectively form an orthogonal set (each is a unit vector) that can be rotated arbitrarily.

In certain embodiments, the 3D image is sliced into different slices to generate multiple 2D images with profiles of biological features thereon. The profiles of biological features may be expression profiles of a biomolecule, staging profiles of tissue abnormality in morphology, or profiles of other biological features. In certain embodiments, the biological features are disease features and can be quantified or assessed. For example, the biological feature may be an expression level of a protein characteristic of a cancer, the TNM staging set by America Joint Committee on Cancer (AJCC), or tumor invasion status that can be determined by methods known in the field of clinical medicine.

Figure 4A:
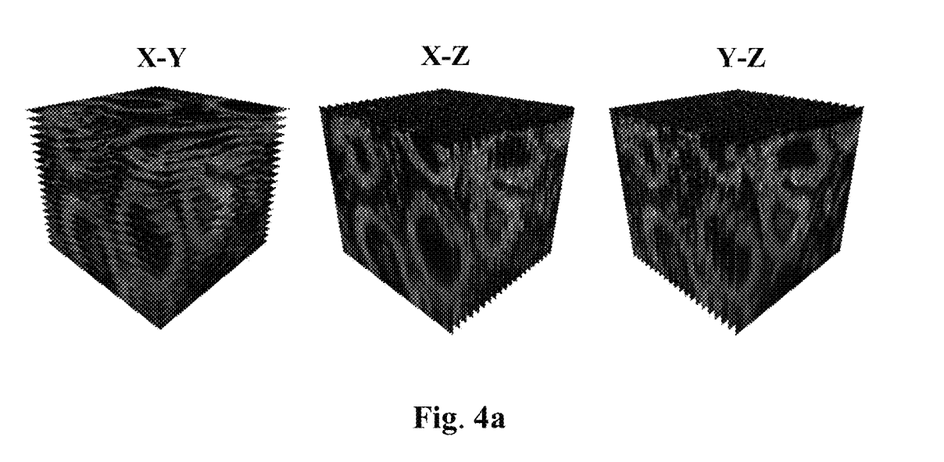
FIG. 4a shows virtual slicing of a 3D image of a normal breast tissue specimen in the direction of an XY-plane, an XZ-plane, or a YZ-plane.
Figure 4B:
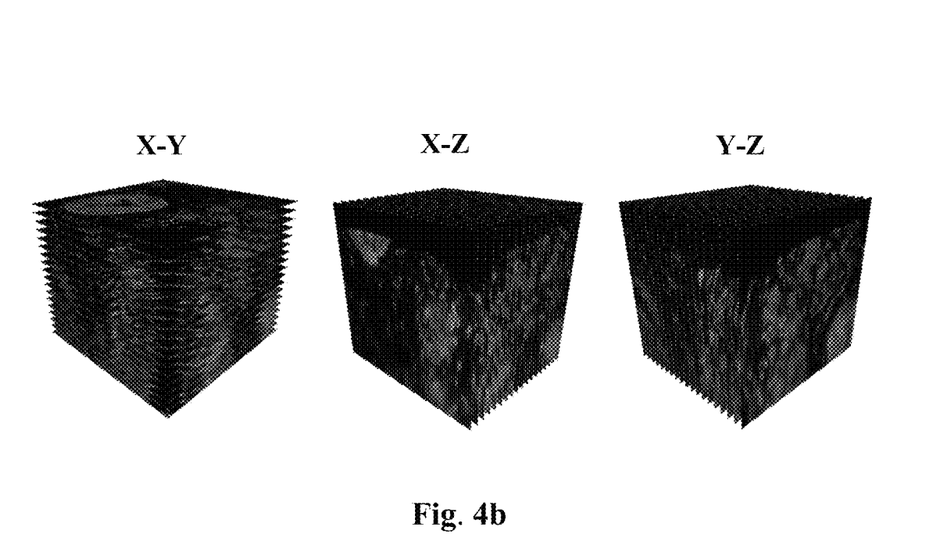
FIG. 4b shows virtual slicing of a 3D image of a breast cancer tissue specimen in the direction of an XY-plane, an XZ-plane, or a YZ-plane.

Diseased tissue, especially tumor/cancer tissue, is heterogeneous. Heterogeneity makes a diseased tissue look significantly different when viewed in different directions. Reference is made to FIGS. 4a and 4b, which illustrate virtual slicing of 3D images in different directions. In FIG. 4a, from left to right, a 3D image of a normal breast tissue specimen is sliced in the direction of an XY-plane, an XZ-plane, or a YZ-plane. The normal breast tissue specimen was collected from a healthy individual and further cleared and labeled with fluorescence dyes for labeling cell membrane and cell nuclei. In FIG. 4b, from left to right, a 3D image of a breast cancer tissue specimen is sliced in the direction of an XY-plane, an XZ-plane, or a YZ-plane. The breast cancer tissue specimen was collected from a breast cancer patient and further cleared and labeled with fluorescence dyes for labeling cell membrane and cell nuclei. It is apparent that in FIG. 4b, the 3D image of breast cancer tissue looks different when viewed from the XY-, XZ-, or YZ-plane. In contrast, the 3D image of the normal breast tissue in FIG. 4a displays similar patterns when viewed in the XY-, XZ-, or YZ-plane.

Next in step (d), a target 2D image is identified among the plurality of 2D images with respective profiles of biological features. Since one specific 2D image in a batch of 2D images may be defined by a distance value of D1, which refers to the distance between said 2D image and one predetermined surface of the 3D image, the identification of a target 2D image can yield a definite D1 value. This D1 value indicates not only the location of the target 2D image in the 3D image but also the location of a particular portion corresponding to the target 2D image in the tissue specimen. Therefore, the D1 value can be used to assist preparing a particular tissue section from a tissue specimen.

Figure 5A:
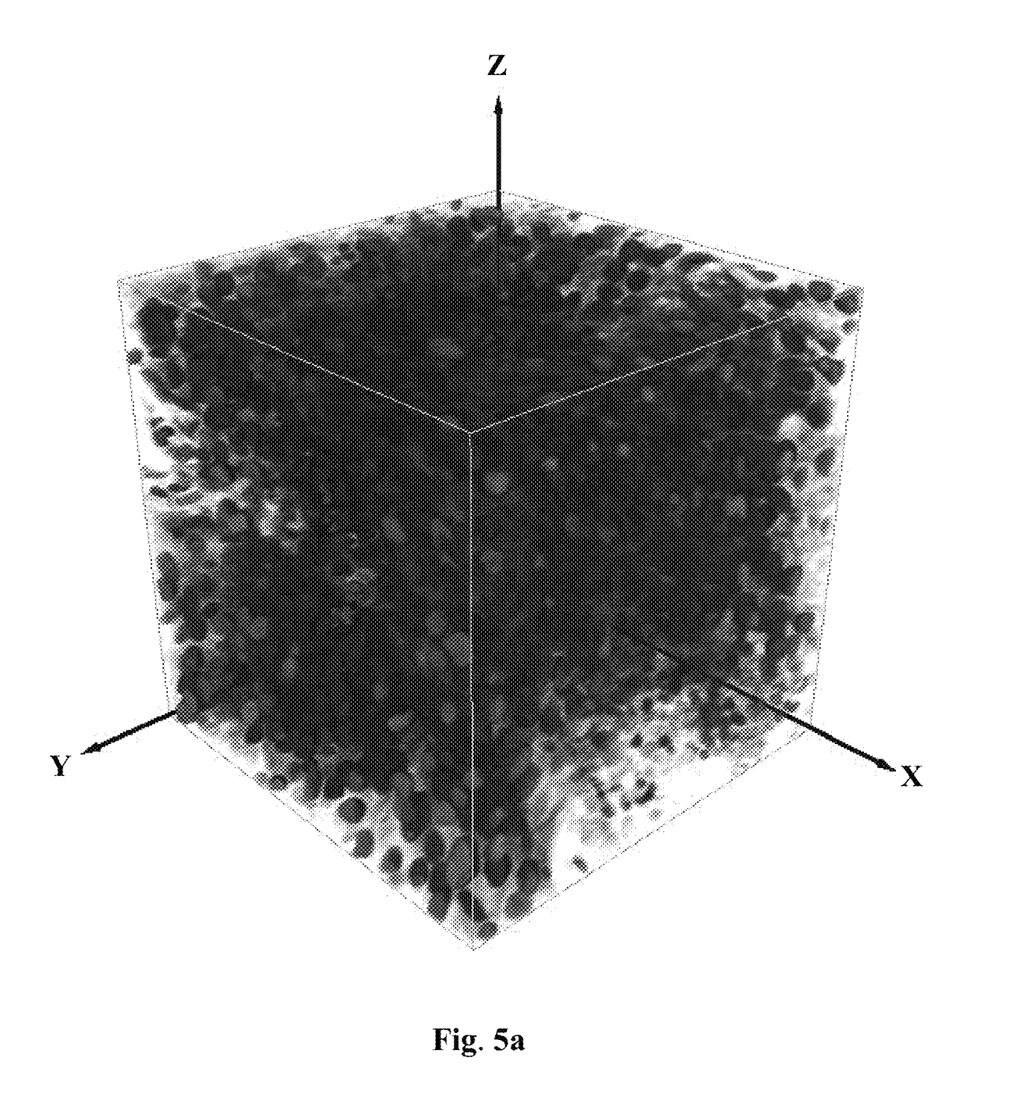
FIG. 5a is a 3D image of a lung tissue specimen; the specimen was labeled with two fluorescence dyes for labeling cell nuclei and cell membrane, respectively, and also labeled with an anti-thyroid transcription factor 1 (TTF-1) antibody that was recognized by a fluorescence dye-conjugated secondary antibody.

Reference is made to FIG. 5a, which is a 3D image of a human lung tissue specimen. The specimen was cleared, followed by being labeled with a fluorescence dye for labeling cell nuclei (displayed in red), a fluorescence dye for labeling cell membrane (displayed in blue), and an anti-thyroid transcription factor 1 (TTF-1) antibody that was recognized by an Alexa Flour 555 (a fluorescence dye)-conjugated secondary antibody (displayed in green). TTF-1 is routinely applied in the diagnostic evaluation of suspected lung cancers as a predictive and prognostic marker. The lung cancer may be graded in four grades as: Grade 1 (also denoted as +), 6% to 25% of tumor cells are TTF-1 positive; Grade 2 (also denoted as ++), 26% to 50% of tumor cells are TTF-1 positive; Grade 3 (also denoted as +++), 51% to 75% of tumor cells are TTF-1 positive; and Grade 4 (also denoted as ++++), more than 75% of tumor cells are TTF-1 positive.

To identify and further assess the biological features such as protein expression levels or tumor region in a 3D image, one straight-forward approach is to adopt 3D feature recognition algorithms, such as 3D convolutional neural network (CNN). However, execution of such algorithms involves expensive computing infrastructure, which limits the application of 3D image analysis. Moreover, these algorithms can only identify certain features in a 3D image, but they cannot extract the most representative 2D images that qualify as a clinical diagnostic basis. Therefore, analyzing 2D image slices with 2D image-based feature recognition algorithms instead of analyzing the 3D image is more appropriate in the field of clinical diagnosis.

Figure 5B:
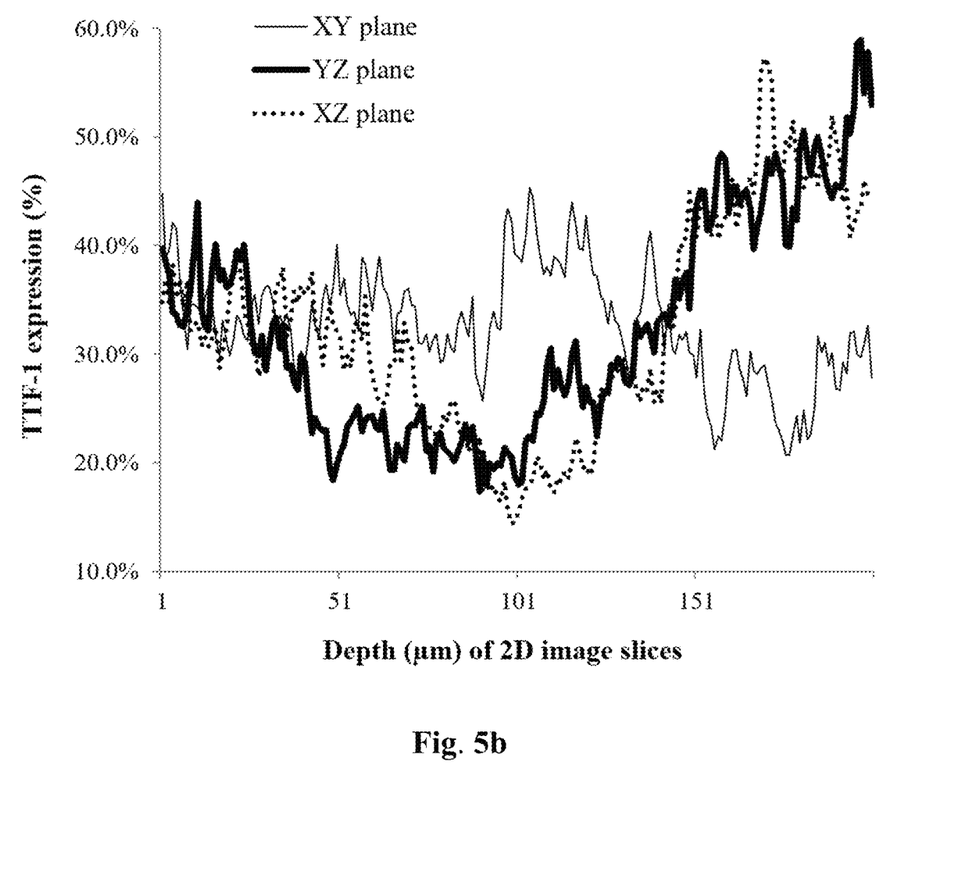
FIG. 5b shows TTF-1 expression in each 2D image among three batches of 2D images, wherein each batch of 2D images were generated by slicing the 3D image of FIG. 5a at different depths in the direction of a XY-plane, a YZ-plane, or a XZ-plane (i.e., along a Z-axis, an X-axis, or a Y-axis, respectively)
Figure 5C:
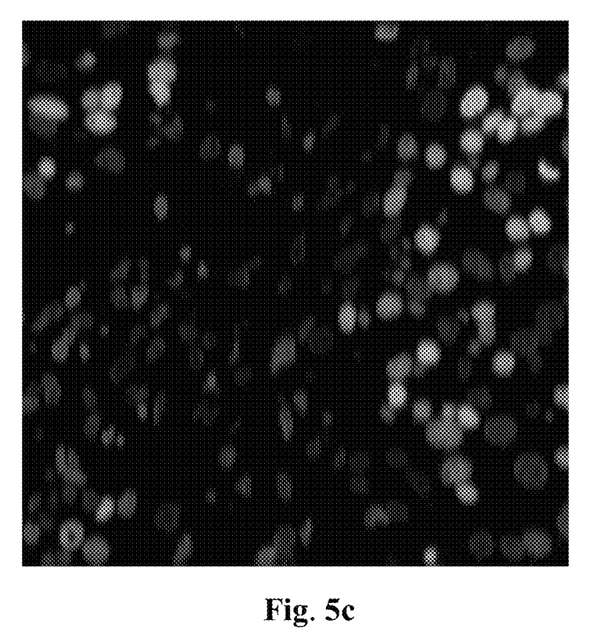
FIG. 5c shows the 2D image sliced in the direction of the XY-plane and displaying the maximum TTF-1 expression.
Figure 5D:
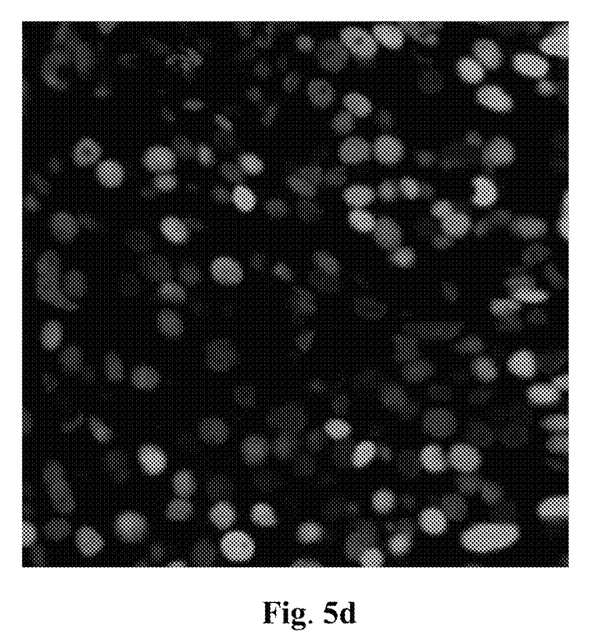
FIG. 5d shows the 2D image sliced in the direction of the YZ-plane and displaying the maximum TTF-1 expression.

The 3D image in FIG. 5a was virtually sliced into multiple batches of 2D images in the direction of a XY-, XZ- or YZ-plane, and TTF-1 expression level in each 2D image among each batch of 2D images was determined as a cell count ratio of TTF-1 positive cells to total cells. One specific 2D image in one specific batch of 2D images may be defined by the distance D1 between said 2D image and a predetermined surface of the 3D image. For example, D1 may be the vertical depth (μm) of a 2D image below the top surface of a 3D image. As shown in FIG. 5b, TTF-1 expression (expressed in percentage) varied between the 2D images sliced at different depths in the direction of the YZ-plane, and the 2D image with the maximum TTF-1 expression can be identified to be 197 μm below the top surface of the 3D image. Similarly, among the 2D images sliced at different depths in the direction of the XY- or XZ-plane, the 2D image with the maximum TTF-1 expression can be identified. Relevant results are shown in Table 1.

According to Table 1, the average TTF-1 expression was similar among different batches of 2D images, but the maximum TTF-1 expression differed significantly, revealing the heterogeneity of tumor tissue. Moreover, by pathologists' microscopic inspection of the tissue specimen, the three 2D images with the maximum TTF-1 expression were validated to represent lung cancer morphology. Accordingly, each of the three 2D images may be elected as a target 2D image. Preferably, the 2D image sliced at a depth of 197 μm (i.e., value D1) in the direction of YZ-plane (i.e., along the X-axis) was elected as a target 2D image.

TABLE 1

| | XY-plane | YZ-plane | XZ-plane |
|---|---|---|---|
| Average TTF-1 expression (%) | 32.7% | 32.4% | 32.5% |
| The depth of the 2D image with the maximum TTF-1 expression | 104 | 197 | 170 |
| Cell counts in the 2D image with the maximum TTF-1 expression (TTF-1 positive cells/total cells) | 63/139 | 102/173 | 87/152 |
| Maximum TTF-1 expression (%) | 45.3% | 59.0% | 57.2% |
| Grade of lung cancer based on the maximum TTF-1 expression | ++ | +++ | +++ |

Once a target 2D image is identified and a D1 value is obtained, a tissue section encompassing the structural characteristics revealed in the target 2D image can be cut out from the cleared and labeled tissue specimen. According to steps (e) and (f) of the disclosed method, the cleared and labeled tissue specimen is processed to form a hardened tissue specimen so that it can be cut without distortion. Subsequently, the hardened tissue specimen is cut near a predetermined site that varies depending on D1. More specifically, the predetermined site is separated by the distance D1 from a surface of the hardened tissue specimen that corresponds to the predetermined surface of the 3D image. One example of said corresponding surface is the top or bottom surface of the hardened tissue specimen.

The hardened tissue specimen may be prepared by, but not limited to, embedding the tissue specimen in an embedding medium such as paraffin wax or cooling the tissue specimen below a temperature of −5° C. The hardened tissue specimen is then transferred to a microtome to be sliced near the predetermined site. Microtome is a slicing apparatus to create micrometer thin slices of materials. A conventional microtome includes an adjustable specimen holder that can hold the specimen and adjust specimen position and orientation, a movable knife that can be moved to an optimal sectioning position in relation to the specimen, and other operating elements for additional functions such as setting section thickness and mechanical trimming. In certain embodiments, the hardened tissue specimen is sliced by a conventional microtome at the predetermined site to yield one tissue section. In other embodiments, the hardened tissue specimen is sliced serially from 1-15 μm above the predetermined site to 1-15 μm below the predetermined site to yield two or more tissue sections, among which a most representative tissue section may be chosen after being stained and examined by pathologists.

The disclosed method may further include removing the labeling agent from the cleared and labeled tissue specimen before step (e) or removing the labeling agent from the tissue section after step (f). In the case where the labeling agent is removed after step (f), the labeling agent may be stripped by immersing the tissue section in a stripping buffer. One example of the stripping buffer is a Tris buffer containing 0.8% 2-mercaptoethanol and 2% SDS. The immersion may be conducted at room temperature or at an elevated temperature. In one preferred embodiment, the tissue section is first deparaffinized with xylene (or d-limonene, sold under the name Hemo-De) and alcohol, followed by being rinsed with PBS at room temperature. The tissue section is then immersed in stripping buffer at about 56° C. for 45 minutes and washed with PBS.

The disclosed method may further include staining the tissue section to obtain a stained tissue section after the labeling agent is removed. Tissue staining may be accomplished by staining methods well-known in the art. Examples of the staining methods include, but not limited to, H&E staining, immunohistochemistry immunofluorescence (IF) staining, and fluorescence in situ hybridization (FISH) staining.

In one embodiment where IHC is conducted, tissue sections are stained first with a primary antibody at 4° C. for about 12 hours and subsequently with a chromogenic enzyme-conjugated secondary antibody at room temperature for about 30 minutes. Thereafter, the tissue sections are immersed in a chromogen solution at room temperature for about 5 minutes. Finally, the tissue sections are counterstained with hematoxylin at room temperature for about 4 minutes and washed with double distilled water.

In sum, the disclosed method utilizes a 3D histopathology imaging method with reduced image losses to generate a high-fidelity 3D image for a tissue specimen and employs virtual image slicing and 2D image-based feature recognition algorithms to analyze the structure of the tissue specimen prior to physical sectioning, and eventually accomplishes collection from the tissue specimen a tissue section encompassing pre-identified histopathological features. Since the 3D image generation process in the disclosed method does not involve slicing a tissue specimen into segments, it can be expected that less, or even no, image losses can be achieved. Furthermore, analysis of the 2D images that are sliced along multiple coordinate axes results in abundant information, enabling medical staffs to make more reliable diagnostic decisions and provide more appropriate therapeutic recommendations. For example, a doctor may rely on HER2 expression profiles obtained from 2D images to determine a patient's eligibility for Herceptin (trastuzumab) therapy. Accurate assessment of HER2 status can ensure that only patients who may benefit from Herceptin therapy receive said treatment.

The method disclosed herein may be performed on a platform including a 3D histopathology imaging system connected to a microtome. The 3D histopathology imaging system includes a microscopy and a processor. The microscopy may be a conventional microscopy that can establish a 3D image of a tissue specimen. The processor is any device that can implement computer instructions. Particularly, the processor is configured to perform an image slicing procedure on the 3D image to generate a plurality of 2D images, to identify one target 2D image, and to yield a distance value of D1. The processor may be, but not limited to, a microprocessor, a microcontroller, or a central processing unit (CPU). The processor may be included in a computer, which further includes memory units for storing computer instructions. The microtome may be a conventional microtome that can cut a specimen at a predetermined site.

Example 1

Preparation of a Breast Tissue Section from a Breast Tissue Specimen

A fresh breast tissue specimen was collected from a female patient likely to suffer from breast cancer. The tissue specimen, first fixed with 4% formaldehyde, was then permeated with 0.1-1% Triton X-100. Subsequently, the tissue specimen was stained with SYTO 16 and DiD to label cell nuclei and cell membrane, respectively. Each labeling was carried out at room temperature for 8 hours. The labeled specimen was then immersed in an aqueous clearing agent at room temperature for about 8 hours. The cleared and labeled tissue specimen, with a thickness of about 150 μm, was imaged from the top surface to the bottom surface with a LSCM system (LSM780; Zeiss) to obtain about a hundred serial 2D images of the specimen that were then used to generate a 3D image of the specimen. The lateral resolution (in the X and Y directions) was less than 1 μm and the axial resolution (in the Z direction) was less than 2 μm.

Figure 6A:
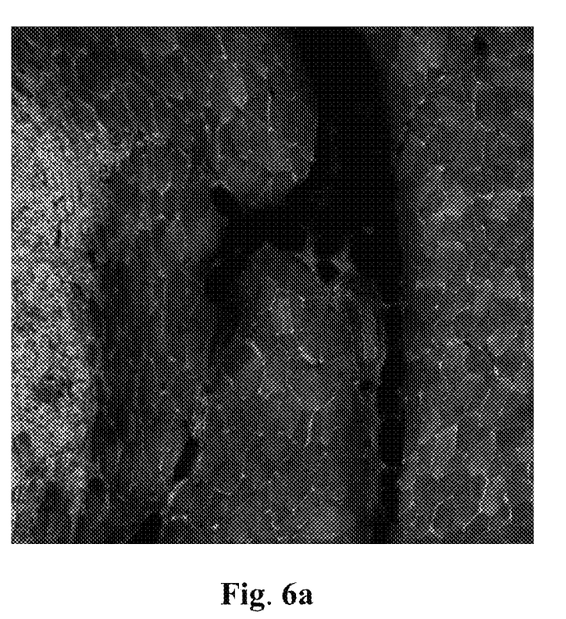
FIG. 6a is a 2D image obtained at a depth of 30 μm below the top surface of a 3D image of a breast tissue specimen.
Figure 6B:
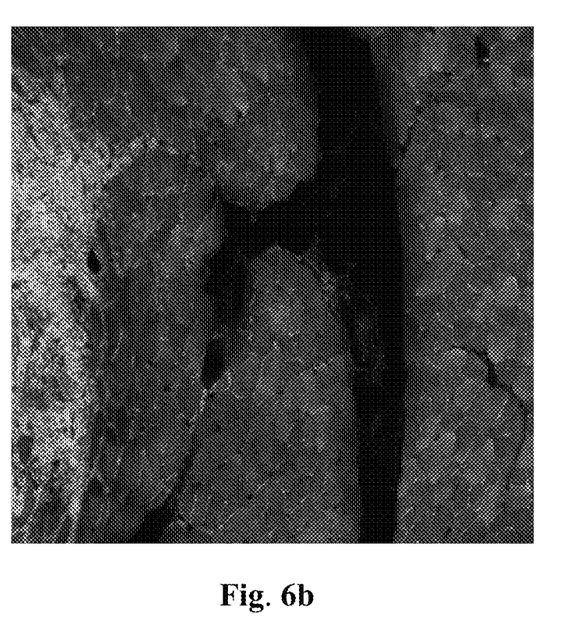
FIG. 6b is a 2D image obtained at a depth of 60 μm below the top surface of a 3D image of a breast tissue specimen.
Figure 6C:
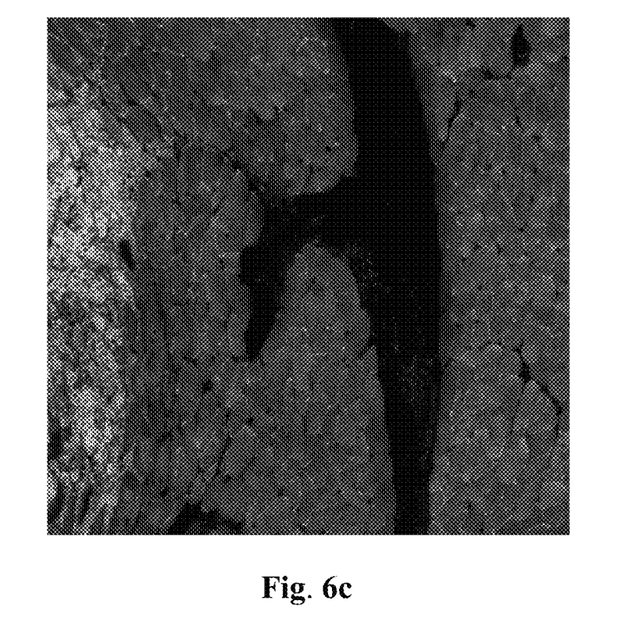
FIG. 6c is a 2D image obtained at a depth of 90 μm below the top surface of a 3D image of a breast tissue specimen.
Figure 6D:
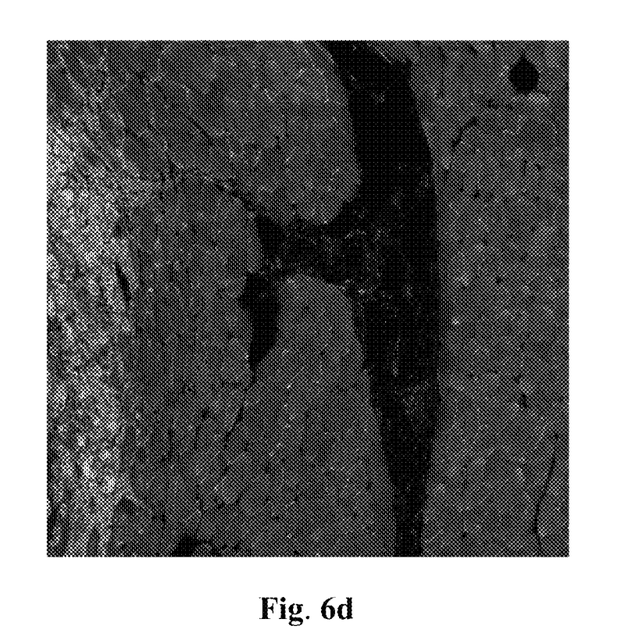
FIG. 6d is a 2D image obtained at a depth of 120 μm below the top surface of a 3D image of a breast tissue specimen.
Figure 6E:
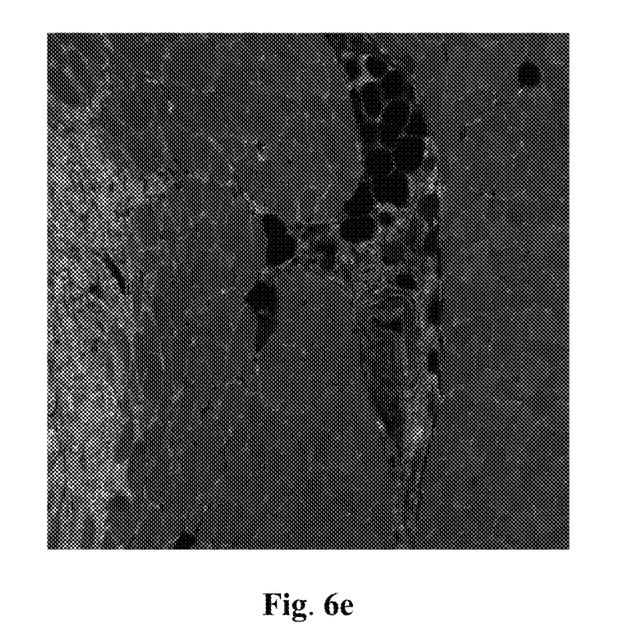
FIG. 6e is a 2D image obtained at a depth of 150 μm below the top surface of a 3D image of a breast tissue specimen.
Figure 6F:
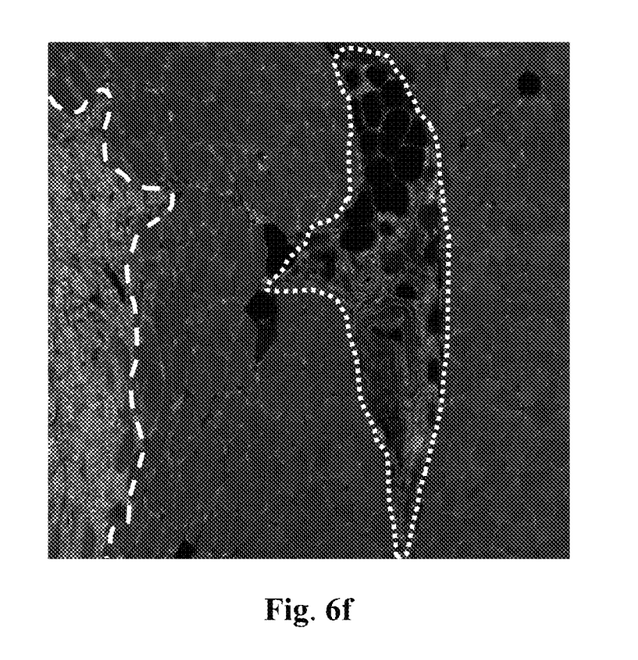
FIG. 6f is a replica of FIG. 6e, where the stroma and the tumor margin are outlined by a dotted line and a dashed line, respectively.

The 3D image was virtually sliced along a Z-axis to generate a batch of 2D images that were then examined by a pathologist to identify the image displaying stroma near tumor margin. This feature was of interest because clinical studies have shown that the morphology of stroma is related with the risk of metastasis. FIGS. 6a-6e respectively show the 2D images sliced from a depth of 30 μm, 60 μm, 90 μm, 120 μm, and 150 μm below a top surface of the 3D image. FIG. 6f is a replica of FIG. 6e, where the stroma and the tumor margin are outlined by a dotted line and a dashed line, respectively. Among these images, stroma was observed only in FIG. 6e. As such, FIG. 6e was identified to be the target 2D image. Since FIG. 6e was 150 μm deep below the top surface of the 3D image, the distance value D1 was set to be 150 μm from the top surface of the 3D image.

Figure 6G:
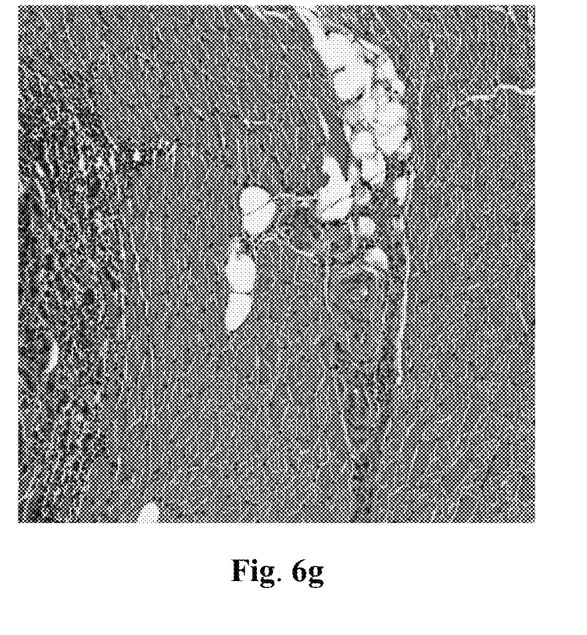
FIG. 6g is a microscopic image of a H&E-stained section encompassing the histopathological features revealed in FIG. 6e.

Subsequently, the specimen was dehydrated and embedded in paraffin. The embedded specimen was then sliced serially by a sliding microtome (pfm Slide 2003) near a site 150 μm deep below a top surface (corresponding to said top surface of the 3D image) of the embedded specimen. The slicing was performed 3-7 times to obtain multiple 5 μm-thick tissue sections, among which one tissue section was collected to prepare a stained tissue section according to H&E staining procedures known in the art and imaged by MoticEasyScan digital slide scanner (Motic, San Francisco, US). FIG. 6g is a microscopic image of the H&E-stained section. It is apparent that FIG. 6g and FIG. 6e are similar in histomorphology, demonstrating that the disclosed method is useful in direct preparation of the tissue sections with pre-identified histopathological features.

What is claimed is:

1. A method for preparing a tissue section, comprising the steps of:
   (a) treating a tissue specimen with a clearing agent and at least one labeling agent for labeling a cellular component so as to obtain a cleared and labeled tissue specimen, wherein the clearing agent is an aqueous clearing agent having a refractive index of 1.33-1.55;
   (b) generating a three-dimensional (3D) image of the cleared and labeled tissue specimen;
   (c) performing an image slicing procedure on the 3D image to generate a plurality of two-dimensional (2D) images;
   (d) in response to the image slicing procedure on the 3D image, identifying a target 2D image among the plurality of 2D images to obtain a distance value of D1, wherein D1 is the distance between the target 2D image and a predetermined surface of the 3D image;
   (e) preparing a hardened tissue specimen from the cleared and labeled tissue specimen; and
   (f) based on the target 2D image identified from among the plurality of 2D images and the obtained distance value D1, cutting the hardened tissue specimen near a predetermined site to obtain a tissue section, wherein a value of the distance between the predetermined site and a surface of the hardened tissue specimen that corresponds to the predetermined surface of the 3D image is the distance value D1.

2. The method of claim 1, wherein the labeling agent is a fluorescence dye, or a conjugate of a fluorescence dye and a molecular probe selected from the group consisting of an agonist, an antagonist, an antibody, an avidin, an oligonucleotide, a lipid nucleotide, and a toxin.

3. The method of claim 1, wherein in step (a) the tissue specimen is embedded in an embedding material.

4. The method of claim 1, further comprising removing the labeling agent from the tissue section after step (f).

5. The method of claim 4, further comprising staining the tissue section to obtain a stained tissue section after the labeling agent is removed.

6. The method of claim 1, wherein the 3D image is generated by using a microscopy to scan the cleared and labeled tissue specimen.

7. The method of claim 1, wherein in the image slicing procedure, the 3D image is sliced along one axis selected from three mutually perpendicular axes of the 3D image.

8. The method of claim 1, wherein the cellular component is a cell membrane, an organelle, or a biomolecule.

9. The method of claim 8, wherein the target 2D image is identified by measuring an expression level of the biomolecule in each 2D image among the plurality of 2D images.

10. The method of claim 1, wherein the target 2D image is identified by measuring a proportion of cells with abnormal morphology relative to total cells in each 2D image among the plurality of 2D images.

11. The method of claim 1, wherein the clearing agent and the labeling agent are included in a clearing composition, and the clearing composition further includes a permeating agent.

12. The method of claim 11, wherein the clearing agent includes a 3refractive index matching material selected from the group consisting of a radiocontrast agent, a monosaccharide, an oligosaccharide, and any combinations thereof.

13. The method of claim 11, wherein the permeating agent is a surfactant selected from the group consisting of Triton X-100, Tween-20, Tween-80, sodium dodecyl sulfate (SDS), n-dodecyl-p-d-maltoside (DDM), urea, 3-[(3-cholamidopropyl) dimethylammonio]-1-propanesulfonate (CHAPS), sodium deoxycholate, and any combinations thereof.

* * * * *